United States Patent [19]

Gutierrez

[11] 4,443,191

[45] Apr. 17, 1984

[54] APPARATUS FOR THE CONFECTION OF MAXILLAR MODELS THROUGH CEPHALOMETIC ANALYSIS

[75] Inventor: Antonio M. Gutierrez, Havana, Cuba

[73] Assignee: Empresa Cubana Exportadora E Importadora de Productos Medicos, Havana, Cuba

[21] Appl. No.: 429,033

[22] Filed: Sep. 30, 1982

Related U.S. Application Data

[63] Continuation of Ser. No. 184,071, Sep. 4, 1980, abandoned.

[51] Int. Cl.³ .............................................. A61C 11/00
[52] U.S. Cl. ...................................................... 433/56
[58] Field of Search ...................................... 433/55, 56

[56] References Cited

U.S. PATENT DOCUMENTS 3,048,923 8/1962 Franwick .
3,409,986 11/1968 Freeman .

*Primary Examiner*—Robert Peshock
*Attorney, Agent, or Firm*—Lackenbach, Siegel, Marzullo, Presta & Aronson

[57] ABSTRACT

An apparatus for the production of maxillar models through cephalometric analysis with auxiliary graduated occlusal plane by simplifying the construction of maxillar models and its anatomic relation, obtaining greater exactness in the correction of the dentomaxillofacial anomalies and reducing the time of confection of the models. The apparatus is formed of a single base having two towers set with condylar elements that support an upper section that holds the condylar movables. The base and the upper section support both the mandibular and the palatal plates with their platforms. The occlusal plate is placed between these two plates resting over two leading rods. An articulated ruler with a level is used for the transference of cephalometric angles, planes and points.

8 Claims, 4 Drawing Figures

APPARATUS FOR THE CONFECTION OF MAXILLAR MODELS THROUGH CEPHALOMETRIC ANALYSIS

This is a continuation of application Ser. No. 184,071, filed Sept. 4, 1980 and now abandoned.

BACKGROUND OF THE INVENTION

The present invention is directed to the fields of Prosthodontics, Orthodontics, Maxillofacial Surgery specially in the branch of dentomaxillofacial anomalies where the use of the apparatus is obligatory for the study and analysis of these anomalies.

From the existing equipment, a number of things are known. For example, the National Gnathostat apparatus for the confection of static maxillar models clinical references are taken such as: the E-E-P (ear-eye plane), the R-M-P (raphe-median plane) and the O-P (orbital plane) of Simon. These static patterns are used in the diagnosis of dentobuccal deviation and anomalies of the mentioned planes. The above is noted by J. A. Salzmann, Orthodontics, Practice and Technics, Lippincott Co., 1957, Pgs. 211–216.

Also known is the method of outlining dental-alveole patterns according to the planes and points of the cephalometric analysis using ruler, compass, scissors, knives to measure and cut the patterns in accordance with this analysis. See, Sassouni, Orthodontics in Dental Practice, Mosby Co., St. Louis, 1971, Pgs. 253–259.

The method of outlining the dental-alveole patterns with reference to the points and planes of the cephalometric analysis is made by cutting the base of the model according to the mandibular plane; the base of the upper model is outlined according to the palatal plane; the anterior part of the upper model is delimited by the anterior nasal spine and the anterior part of the lower model is delimited by the pogonio; the posterior borders of both models are outlined according to a perpendicular to the plane of Frankfort. All these cuts are made by measurements and studies of the cephalometric analysis.

The maxillar models made through cephalometric analysis without the assistance of an apparatus is not completely exact since the transcription of measurements and angles of the planes is frequently made by cutting counter-drawings of these planes and angles in cardboard, outlining the dental alveole casts by comparison, and using the teleradiography, the patterns are shaped and scraped to obtain reference of the planes described above. Besides, the patterns obtained are only connected by the dental joint which makes difficult and inexact the measurements for possible corrections.

SUMMARY OF THE INVENTION

The main object is to overcome the defects of the present invention.

Another object of the invention is to construct maxillar models through the cephalometric analysis and the graduated occlusal plane of anatomic size and shape in lesser time.

A further object is to transfer points, planes and angles of this analysis to an apparatus obtaining models dynamically adjoined and articulated in craniofacial position in the 3 dimensions of space.

Still a further object is to measure the position and relations obtained and the corrections projected in any of the planes.

The inventive apparatus has been found useful for the preparation of prosthesis because of its interchangeable plates.

In accordance with the present invention there is provided an apparatus with both condylar elements and plates (palatal, occlusal and mandibular) adaptable to the three planes of space thus permitting the anatomical construction and adjoining of maxillar models by the use of an articulated ruler with a level to transfer the points, planes and angles of the cephalometric analysis and the graduated occlusal plane to the apparatus.

More particularly, there is provided an apparatus for the production of maxillar models through cephalometric analysis simplifying the construction of maxillar models and its anatomic relation, obtaining greater exactness in the correction of the dentomaxillofacial anomalies and reducing the time of confection of the models. The apparatus is formed of a single base having two towers set with condylar elements that support an upper section that holds the condylar movables. The base and the upper section support both the mandibular and the palatal plates with their platforms. The occlusal plate is placed between these two plates resting over two leading rods. An articulated ruler with a level is used for the transference of cephalometric angles, planes and points. The scales of the apparatus permit measurement of the position and motion of its movable elements.

The invention can be best understood with respect to the specification, claims and drawings.

DESCRIPTION OF THE INVENTION

Figure 1:
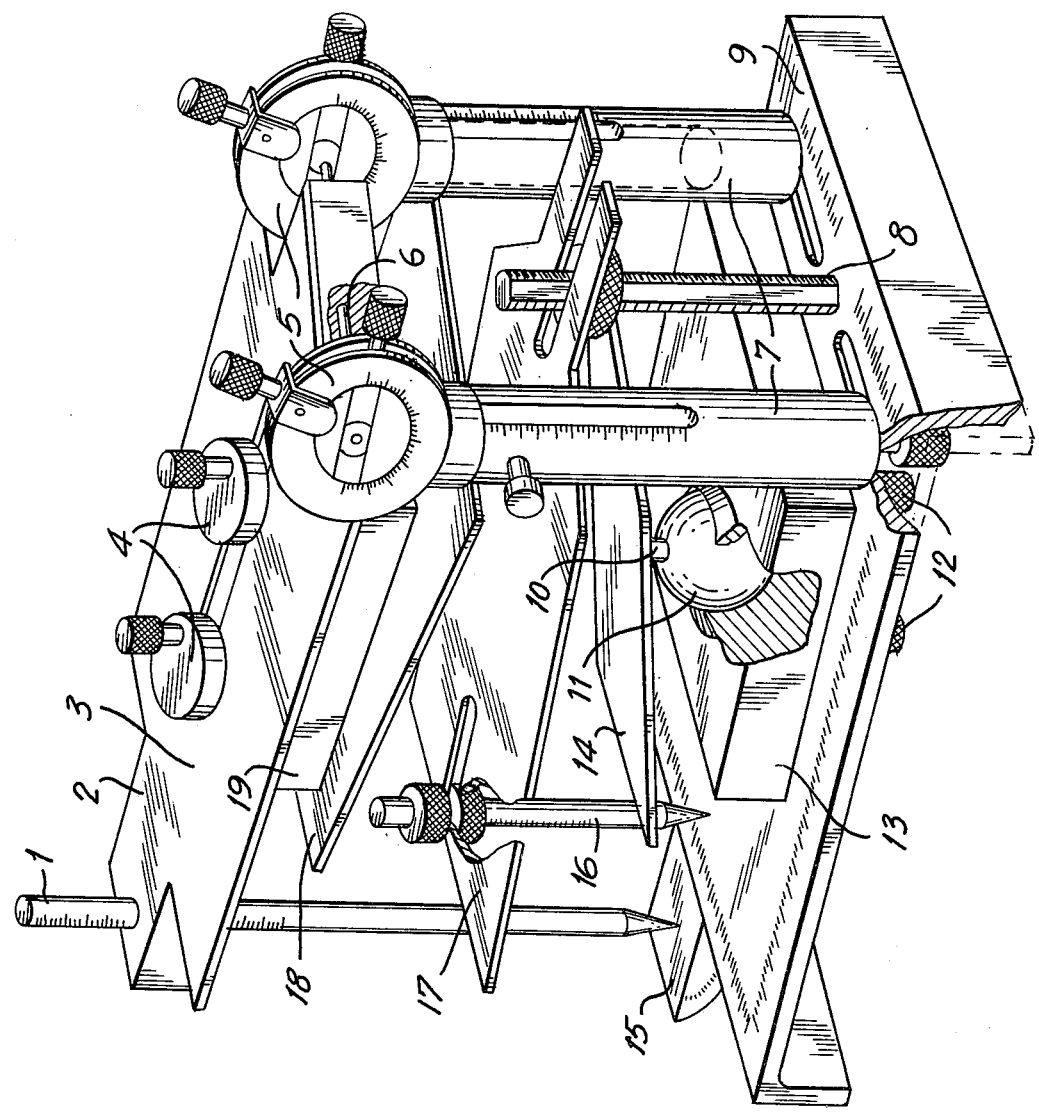
FIG. 1 is an axomonetric view of the apparatus.

The apparatus (FIG. 1) consists of one single base (9). In its posterior part and at both sides of the median line are set two towers (7) that may be adjusted by means of the scale in the base according to the distances right-condyle sagittal plane (33) and left-condyle sagittal plane (35) of FIG. 3. In the upper part of both towers (7) the condylar elements (5) are telescopically set that may be adjusted according to the condyles position. The condylar elements (5) have condylar guides with fixing screws.

The base (9) and the upper section (3) have a slot in their median line with an antero-posterior direction where the eccentrics (4,12) slide and are fixed. These eccentrics support the platforms (19,13) which by means of a ball joint (11) placed in its middle, sustain the mandibular (14) and palatal (18) plates.

Figure 2:
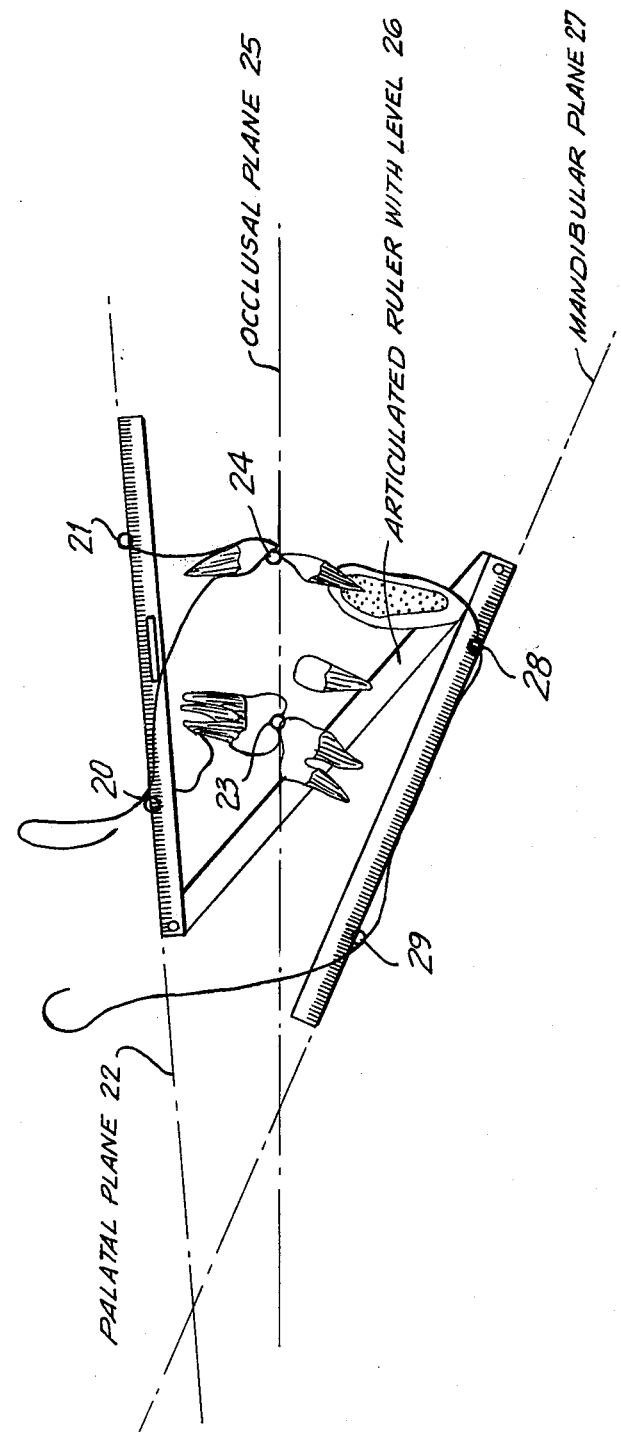
FIG. 2 is a tracing of a lateral teleradiography with its cephalometric analysis.
Figure 4:
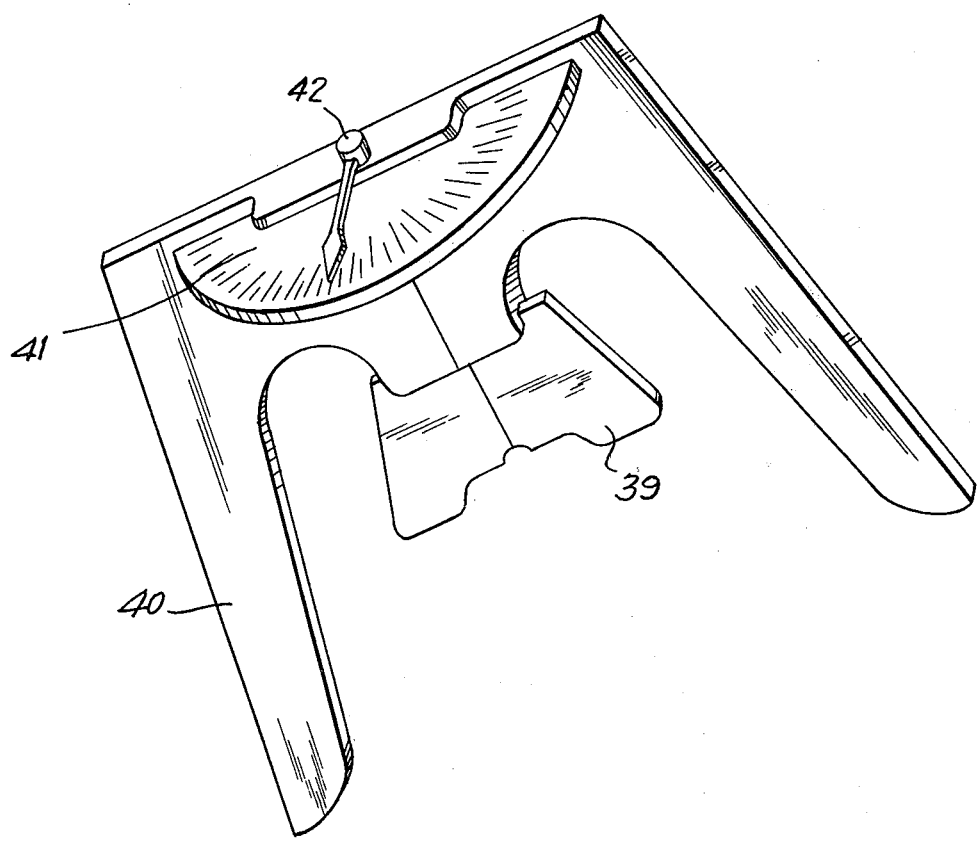
FIG. 4 is an axomonetric view of the graduated occlusal plane.

The rod (10) that joins the sphere (11) with the corresponding plates (14,18) permits adjustment of the required height. With the articulations and adjustment of the height, it is possible to place the plates (14,18) according to the palatal (22) and the mandibular (27) planes of FIG. 2. The occlusal plate (17) is used to put into position the inferior dental cast in cephalometric relation with the angulation determined by the graduated occlusal plane (FIG. 4). It is placed and adjusted in the leading rods (8,16) guided by the level of the ruler (26) which transfers the relation of the mandibular (27)

and occlusal (25) planes of FIG. 2 and the angulation of the occlusal plane (FIG. 4).

The upper section (3) has an elongation (2) with the entrance of the incisal rod (1) which lies in the adaptable incisal guide (15) placed in the anterior part of the base (9).

To obtain the maxillar models the following steps are employed.

1.—Graduated occlusal plane (FIG. 4):

With the head of the patient in horizontal position, the interchangeable occlusal plate (39) is placed in centrical occlusion and sagittal median line. The grades are measured in the graduated semi-circle (41) according to the position of the pendulum (42).

2.—Cephalometric analysis:

In the lateral teleradiography (FIG. 2) the Gonion (29) the menton (28), the highest cuspid (23), the incisal border (24) and the anterior (21) and posterior (20) nasal spine are marked and the mandibular (27), occlusal (25) and palatal (22) planes are outlined.

In the antero-posterior teleradiography (FIG. 3) the right and left Gonion (33,36) and right and left condyles (31, 37) are marked and projection is made of the sagittal plane and the perpendiculars of the different points (32,34,35,38) to the mentioned sagittal.

All the points and planes of the cephalometric analysis are measured with the scale of the ruler (26) of FIG. 2.

3.—Construction of the negative profile:

Over the lateral tracing (FIG. 2) two patterns of thin metal are cut: an inferior pattern delimined by the mandibular (27) and the occlusal planes (25). This profile is marked and cut from its intersection up to approximately two centimeters in front of the mandibular profile obtaining one anterior and one posterior part with the negative mandibular profile (piece for contour). The superior pattern is delimited by the occlusal (25) and the palatal (22) planes from the posterior nasal spine (20) to approximately two centimeters in front of the maxillar profile. This profile is marked and cut to obtain two pieces, one anterior and one posterior with the negative maxillar profile (piece for contour).

4—Preparing the models:

The inferior model is casted in horseshoe shape the height not interfering with the mounting. At labial level of the incisive profile, the gum is pared to arrange the setting of the negative mandibular profile patterns.

The superior model should also be cast with the height not interfering with the mounting. At face level of the incisive profile, the zone of the gum is pared to arrange the setting of the pattern of the negative maxillar profile.

The clinical median line in both models, superior and inferior is marked out.

5.—Transference of planes and points of the cephalometric analysis and the graduated occlusal plane to the apparatus. Use of the cephalometric ruler with level in each of its sections:

With the cephalometric ruler (FIG. 2) the mandibular (27) and the occlusal (25) planes are taken and fixed. Then these are transferred to the apparatus. The mandibular plate (14) is adjusted until the level of the occlusal section of the ruler is in a horizontal position, then fixing the plate (14).

The occlusal plate (17) is placed resting over the occlusal section of the ruler setting into position the leading rods (8, 16) according to the variation of the angle given by the graduated occlusal plane. With the cephalometric ruler, the angles of the mandibular (27) and the palatal (22) planes of FIG. 2 are taken, fixed and transferred to the apparatus adjusting the palatal plate (18) of FIG. 2 fixing its position.

Figure 3:
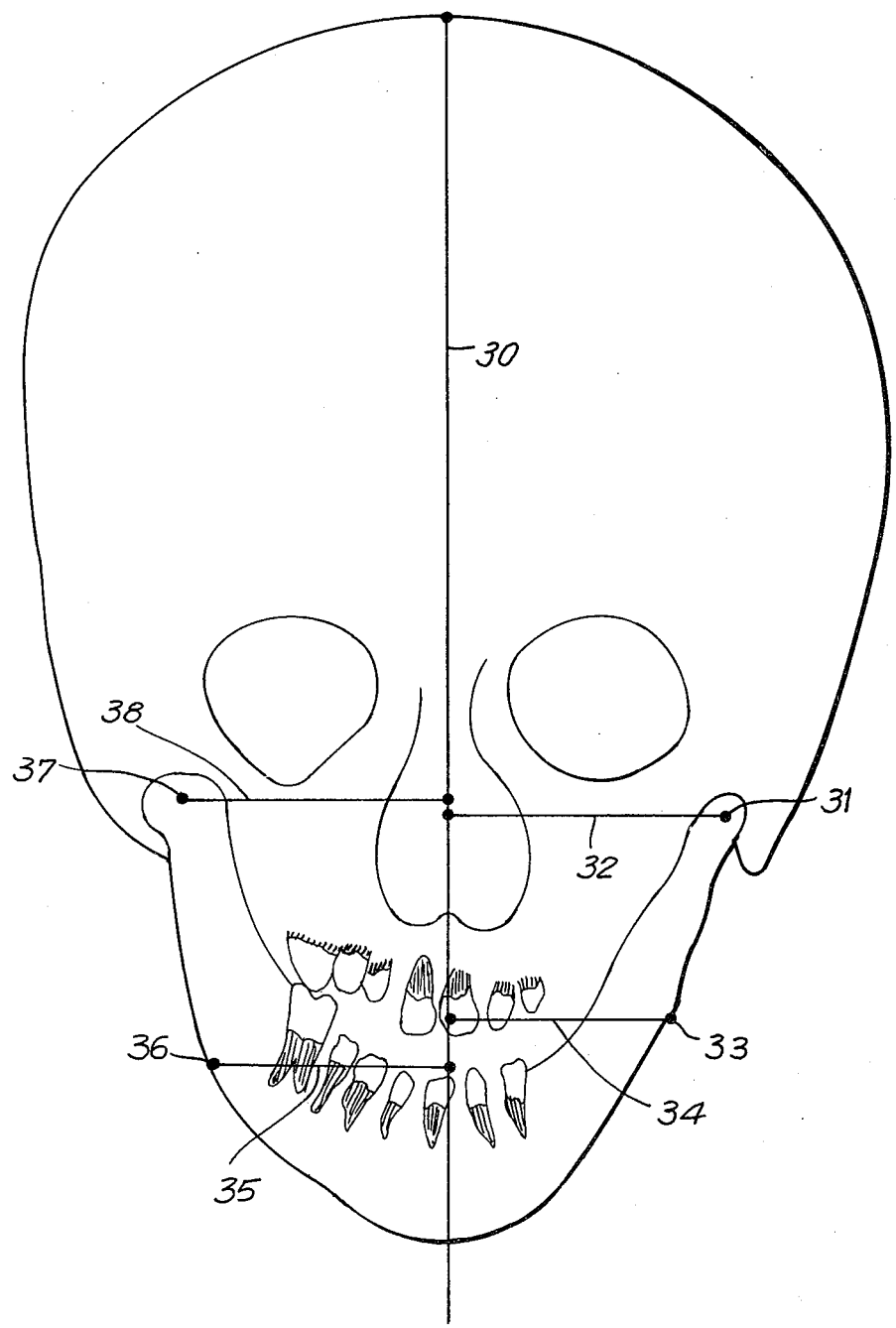
FIG. 3 is a tracing of a postero-anterior teleradiography with its cephalometric analysis.

Both condylar elements (5) of the apparatus (FIG. 1) are placed into position transferring the lengths of the perpendiculars (32,34,35,38) of FIG. 3 by means of the cephalometric ruler.

6.—Construction and setting of maxillar models in the apparatus:

The inferior model is fixed to the occlusal plate (17) correctly adjusted in the antero-posterior and lateral direction. The occlusal plate is placed into position in the apparatus, fixing the model of the mandibular plate (14); and then the occlusal plate is removed.

The superior model is then connected to the inferior model, already fixed by means of a centrical articulation and the superior model is fixed to the palatal plate (18).

To attach the models to the corresponding plates, wax, modeling compounds or plaster may be used.

To make the contour of the mandibular profile, the pattern of the negative mandibular profile is used, placing it over the labial face of the incisive profile and the mandibular plate (14) marking the position of the menton point (28) of FIG. 2 in the plate.

In the same fashion the contour of the maxillar profile is made using the negative maxillar profile marking in the palatal plane (18), the position of the anterior nasal spine point (21) of FIG. 2.

In the mandibular plate (14), the position of the Gonion (29) is marked in antero-posterior direction according to the length of the mandibular plane as from the menton (28) of FIG. 2. In lateral direction, the position of the Gonion (33,36) is marked by the length of the perpendicular (34,35) of FIG. 3.

In the palatal plate (18), the position of the posterior nasal spine (20) is marked as from the anterior nasal spine (21) with the length of the palatal plate (22) of FIG. 2.

BEST MODE OF INVENTION

The apparatus is formed of a single base (9) having two towers (7) set with condylar elements (5) that support an upper section (3) that holds the condylar movables. The base and the upper section support both the mandibular (14) and the palatal (18) plates with their platforms (13,18). The occlusal plate (17) is placed between these two plates resting over two leading rods (8,16). An articulated ruler with a level (26) is used for the transference of cephalometric angles, planes and points.

Many modifications and variations of the present invention are possible in light of the above teachings. It is, therefore, to be understood that within the scope of the appended claims, the invention may be practiced otherwise than as particularly described.

What is claimed is:

1. An apparatus for the production of maxillary and jawbone models from teleradiographics with all of their corresponding osseous and anatomical form and structure including their dimensional relationships through cephalometric analysis comprising: a single base; a pair of towers extending from said single base, said towers being set with condylar means for supporting an upper section; said upper section being provided with condylar movements; said base and said upper section being adapted to support mandibular and palatal plates and their respectively connected sliding ball joint platforms, said platforms which support said models; an occlusal plate is disposed between said mandibular and palatal plates and is positioned over first and second rods; said first rod supporting one end of said occlusal plate and being disposed between said pair of towers, and said second rod supporting the other end of said occlusal plate being disposed at said other end of said occlusal plate opposite said first rod; where cephalometric angles, planes and points may by transferred to said apparatus by means of an articulated cephalometric ruler.

2. An apparatus as claimed in claim 1, wherein: said towers are telescopically formed to move independently in a transverse direction with reference to the base, having in the upper part of each tower a condylar element movable in the vertical direction and able to turn over its axis, said condylar elements resting therein and having respective axes with associated movement and transfer fixed by means of scales.

3. An apparatus as claimed in claim 1 wherein;
said mandibular plate is attached to its inferior platform by means of a telescopic rod and an adjustable ball joint to provide the position of the cephalometric mandibular plane; said palatal plate being similarly attached to its superior platform as is said mandibular plate and being fixed to said upper section.

4. An apparatus as claimed in claim 1, wherein: said respective sliding platforms move in antero-posterior and lateral directions with reference to said base at an angle of approximately 5°, to permit movement of the maxillar model in said plates in three spatial planes.

5. An apparatus as claimed in claim 1, wherein: said occlusal plate is provided with a first slot in a median line to allow said second anterior rod to slide and a second slot is provided in a posterior part of said occlusal plate where said first posterior rod of said base is positioned.

6. An apparatus as claimed in claim 1, wherein: an independently operated auxiliary graduated occlusal plane is provided and defined by a base having in its front median line, a graduated semi-circle scale with a pendulum for permitting measurement of the grades of deviation of a patient's occlusal plane for transference to said apparatus.

7. An apparatus as claimed in claim 6, wherein said ruler is provided with a built-in level.

8. An apparatus as in claim 5, wherein said first and second rods are provided with threaded means and associated knurled threaded nuts for adjusting the elevated position of said occlusal plate.

* * * * *